(12) United States Patent
Wubbeling (10) Patent No.: US 9,060,894 B2
(45) Date of Patent: Jun. 23, 2015

(54) CATHETER SHEATH FOR IMPLANT DELIVERY

(75) Inventor: Martin Wubbeling, Mannheim (DE)

(73) Assignee: C. R. Bard, Inc., Murray Hill, NJ (US)

( * ) Notice: Subject to any disclaimer, the term of this patent is extended or adjusted under 35 U.S.C. 154(b) by 721 days.

(21) Appl. No.: 13/132,816

(22) PCT Filed: Dec. 3, 2009

(86) PCT No.: PCT/EP2009/066315
§ 371 (c)(1),
(2), (4) Date: Aug. 19, 2011

(87) PCT Pub. No.: WO2010/063795
PCT Pub. Date: Jun. 10, 2010

(65) Prior Publication Data
US 2012/0022630 A1    Jan. 26, 2012

(30) Foreign Application Priority Data
Dec. 3, 2008    (GB) .................................. 0822110.3

(51) Int. Cl.
*A61F 2/95*    (2013.01)
*A61F 2/97*    (2013.01)

(52) U.S. Cl.
CPC ... *A61F 2/95* (2013.01); *A61F 2/97* (2013.01); *A61F 2002/9511* (2013.01)

(58) Field of Classification Search
CPC ...... A61F 2/95; A61F 2/97; A61F 2002/9511
USPC ........ 623/1.11–1.13, 1.2–1.23; 606/108, 194;
220/23.9, 23.91, 510, 62.11, 621–622,
220/626, 646, 648, 650, 677, 680, 693;
206/364, 363
See application file for complete search history.

(56) References Cited

U.S. PATENT DOCUMENTS 4,453,875 A * 6/1984 Johnson, Sr. ................... 414/304
5,151,105 A * 9/1992 Kwan-Gett ................... 623/1.32

(Continued)

FOREIGN PATENT DOCUMENTS

WO        9827895 A9    9/2006
WO     2007084762 A3    5/2008

(Continued)

OTHER PUBLICATIONS

PCT/EP2009/066315 filed Dec. 3, 2009 International Preliminary Report on Patentability dated Jun. 7, 2011 and Written Opinion dated Mar. 19, 2010.

(Continued)

*Primary Examiner* — Katrina Stransky
*Assistant Examiner* — Sidharth Kapoor
(74) *Attorney, Agent, or Firm* — Rutan & Tucker, LLP (57) ABSTRACT

There is disclosed herein a tube of material (1) having a seam (12) extending between a proximal end and a distal end, two edges (10a, 10b) of the material meeting and at least partially overlapping along the seam (12) and being sewn together at the seam by stitches (21, 22, 24) of relatively flexible thread (20), the thread of one or more of the stitches (22, 24) passing from a first side (12a) of the overlapped edges (10a, 10b) of material, through both layers of overlapped material, crossing a relatively rigid member (30) which is disposed on a second, opposite side (12b) of the overlapped edges of material, and passing back to the first side (12a). There is further disclosed an implant delivery catheter (40) incorporating the tube of material (1), and associated methods for its manufacture.

20 Claims, 6 Drawing Sheets

(56) References Cited

U.S. PATENT DOCUMENTS

| | | | |
|---|---|---|---|
| 5,653,748 A | 8/1997 | Strecker | |
| 6,015,431 A * | 1/2000 | Thornton et al. | 623/1.14 |
| 6,019,785 A | 2/2000 | Strecker | |
| 6,042,605 A * | 3/2000 | Martin et al. | 623/1.13 |
| 6,302,891 B1 * | 10/2001 | Nadal | 606/108 |
| 6,352,561 B1 | 3/2002 | Leopold et al. | |
| 7,594,926 B2 * | 9/2009 | Linder et al. | 623/1.11 |
| 7,686,783 B2 * | 3/2010 | Jenson et al. | 604/104 |
| 7,896,183 B2 * | 3/2011 | McKenzie | 220/4.34 |
| 8,092,513 B2 * | 1/2012 | Khosravi et al. | 623/1.13 |
| 2007/0233220 A1 * | 10/2007 | Greenan | 623/1.11 |
| 2008/0071343 A1 * | 3/2008 | Mayberry et al. | 623/1.11 |
| 2009/0082842 A1 * | 3/2009 | Glynn | 623/1.11 |
| 2009/0083904 A1 * | 4/2009 | Roston | 4/558 |
| 2012/0130475 A1 | 5/2012 | Shaw | |

FOREIGN PATENT DOCUMENTS

| | | |
|---|---|---|
| WO | 2008140796 A1 | 11/2008 |
| WO | 2012068046 A2 | 5/2012 |

OTHER PUBLICATIONS

PCT/EP2009/066315 filed Dec. 3, 2009 International Search Report dated Mar. 19, 2010.

* cited by examiner

CATHETER SHEATH FOR IMPLANT DELIVERY

PRIORITY

This application is a U.S. national stage application under 35 USC §371 of International Application No. PCT/EP2009/066315, filed Dec. 3, 2009, claiming priority to United Kingdom Patent Application No. 0822110.3, filed Dec. 3, 2008, each of which is incorporated by reference in its entirety into this application.

FIELD OF THE INVENTION

The present invention relates to a tube of material, to associated methods of manufacturing a tube of material, and to an implant delivery catheter incorporating such a tube of material. The tube of material may be of a form that can be used as a releasable outer sheath for delivering expandable or self-expanding implants, such as stents.

BACKGROUND

Numerous implant delivery systems have been devised for conveying and deploying prosthetic implants in the human body. Continued development in the field of material science has enabled an increasingly diverse range of implants to be devised which can be delivered to and implanted non-invasively at a treatment location. Such implants will typically have a low-profile delivery configuration and are expanded to a large-profile operative configuration at the treatment location. These implants can either be expanded mechanically to their operative configuration, for example by the use of balloons or pull-wires to transform the implants from their delivery configurations to their operative configuration, or they may be self-expanding implants which will naturally tend to expand to their operative configurations when released from the constraints of a delivery device.

For deployment of implants into luminal body passageways, catheter based delivery systems have become widely used. A typical catheter based delivery system is provided with an elongate inner shaft, with the implant mounted to the distal end portion of the shaft. An outer sheath surrounds the implant and at least the end portion of the inner shaft, to constrain the implant in its delivery configuration prior to being selectively deployed. In a typical procedure, the distal end of the delivery system is introduced percutaneously into a patient and advanced along a body lumen until the implant at the distal end portion is brought to a treatment location. The outer sheath is then removed to release the implant to be deployed at the treatment location. Because these catheter based delivery systems can be made relatively long and of a small diameter, they are particularly suited for advancement of implants to treatment locations within the human vasculature, the urinary tract and the biliary tree.

Various different arrangements have been devised for removing the outer sheath so as to release the implant for deployment at the treatment location. In one common arrangement, the outer sheath is retractable in a proximal direction relative to the inner shaft, so that the implant can be gradually released as the sheath is retracted, exposing the distal end portion of the inner shaft where the implant is mounted. These systems, however, are often relatively complex in order to provide the system with the necessary functionality. For example, the inner shaft has to be made axially substantially incompressible, so as to allow the shaft to be advanced along a body passage-way as it is pushed into the body from the proximal end. At the same time, the shaft has to be of a small diameter in order to allow it to be advanced through narrow bodily lumens, and has to be highly flexible so as to enable it to pass around the tight curvatures encountered in body passage-ways such as the human vasculature without kinking. The inner shaft also has to resist compression under the influence of the axial tensile force that has to be applied in order to retract the outer sheath. The inner shaft is often provided with a tightly wound compression spring in order to provide the necessary resistance to axial compression but the required flexibility off-axis.

The outer sheath is often responsible for providing the necessary force to constrain the implant in its delivery configuration, in particular where the implant is self-expanding and tends to exert a radially outward force trying to adopt its expanded operative configuration. Not only must the outer sheath resist these radially outward forces, but it must be retractable in a proximal direction, for which purpose it is preferably relatively inextensible in the longitudinal direction. A reinforcing structure, such as braiding, is typically used in the outer sheath to give it the necessary properties of off-axis flexibility during advancement of the catheter to the delivery location, and at the same time the necessary longitudinal strength to be proximally withdrawn for releasing the implant. The use of these reinforcements to the inner shaft and outer sheath, to give these components the necessary structural properties, thus tends to result in an increase in the thickness and overall diameter of the components and the system as a whole, which is contrary to the objective of reducing the system diameter to allow it to be advanced through narrow bodily lumens. Such systems can also be costly and time-consuming to manufacture.

An alternative arrangement for releasing the outer sheath has been devised, which can potentially reduce the axial forces associated with sheath retraction and release of the implant. The sheath is formed as a tube of material, for example ePTFE. This tube of material has the necessary strength and properties to constrain the implant in its delivery configuration. The tube is formed from a sheet of the material, folded so that opposite edges of the sheath meet and form a seam. The seam is then sewn together using a suture thread in a manner in which the thread can be released by pulling on one end of it. In use, the tube of material functions as the outer sheath during advancement of the end portion of the delivery system to a treatment location, at which point the thread is pulled to release the stitching and thus allow the tube of material to separate at the seam, facilitating deployment of the implant constrained therein. The sheet of tube material can then either be retracted along with the delivery system, after the implant has been deployed, or may be attached to the implant and left in situ at the treatment location, held between the implant and the treatment location to form part of the implant. Examples of such an implant deployment apparatus are disclosed in U.S. Pat. No. 6,352,561 B1, which is incorporated by reference in its entirety into this application, to Leopold et al., published on $5^{th}$ Mar., 2002, in which the skilled reader will find examples of different stitching patterns for forming the tube of material as well as discussion of suitable materials for the outer sheath (restraining member 102) and suture or sutures (thread-like coupling member 104).

Such catheter delivery systems are particularly useful for the delivery of balloon-expandable or self-expandable stents and stent grafts, as well as valve implants and the like. With the systems employing a stitched tube of sheet material as the outer sheath, however, there can be a problem that the suture may snap before the thread is fully released from the seam of the tube, or that the stitching may become knotted or tangled at the distal end prior to complete release of the seam. This is a particular risk due to the typical length of catheter delivery systems, along which the proximally extended portion of the suture thread must pass to reach the proximal end of the delivery system where it can be manipulated, typically a meter or more in length, and the tight curvatures around which the delivery system must pass, and in which the implant may be deployed, within human bodily lumens. If the thread snaps or becomes entangled after the stitching has been only partially released, it may not be possible to retract the delivery system without damaging the bodily lumen through which the catheter has been inserted, or to fully deploy the implant. Intervention by open surgery would then be required. On the other hand, if the suture thread is made thicker, to withstand retraction forces without snapping, the overall thickness of the seam will be increased, whilst the potential for entanglement or snagging remains.

U.S. Pat. No. 6,019,785 A, which is incorporated by reference in its entirety into this application, discloses a device for delivering a prosthesis held within a sheath in a delivery configuration. The sheath is held in a retracted delivery configuration by forming stitches of thread material around the outer circumference of the sheath, at a diameter at which the prosthesis internal of the sheath is constrained. In the embodiment of FIG. 7 of U.S. Pat. No. 6,019,785 A, a warp thread 78 is used to secure loops of the thread 75 in place around the circumference of the sheath. However, there is no indication in U.S. Pat. No. 6,019,785 A that the warp thread 78 is of any more or less flexible material than the thread 75 used to form the constraining loops. Moreover, the thread 75 in U.S. Pat. No. 6,019,785 A does not pass from a first side of overlapped edges of material, through both layers of overlapped material, cross a relatively rigid member which is disposed on a second, opposite side of the overlapped edges of material, and pass back to the first side.

WO 2008/140796 A; which is incorporated by reference in its entirety into this application, discloses a stent graft having diameter reducing ties 22, 24 formed so as to progress circumferentially around the sides of the stent graft from one end to the other. The diameter reducing ties 22, 24 are tied to release wires 18, 20, for example as illustrated in FIG. 5A of NO 2008/140796 A. The release wires 18, 20 are stitched into the material of the stent graft, to hold them in the desired position along the length of the stent graft. When the release wires 18, 20 are pulled, they release the diameter reducing ties 22, 24, allowing the stent graft to expand. The relative rigidity or flexibility of the release wires 18, 20 is not mentioned. In WO 2008/140796 A, the suture threads 22, 24 of flexible material are used to form circumferential loops, and not to form stitches along a seam at the overlapping edges of a tube of material.

SUMMARY OF THE INVENTION

According to a first aspect of the present invention, there is provided a tube of material having a seam extending between a proximal end and a distal end, two edges of the material meeting and at least partially overlapping along the seam and being sewn together at the seam by stitches of relatively flexible thread, the thread of one or more of the stitches passing from a first side of the overlapped edges of material, through both layers of overlapped material, crossing a relatively rigid member which is disposed on a second, opposite side of the overlapped edges of material, and passing back to the first side. The relatively rigid member can resist unwanted small radius, high curvature deflection lateral to the seam, although is flexible with larger radius, low curvature deflections of the tube. The relatively rigid member is thus able to be removed from between the stitches which cross it and the second side of the overlapped tube material with certainty and precision, and without risk of breaking as it is manipulated for removal. The relatively flexible thread is able to adopt the small radius, high curvature needed to form a stitch, but need only be strong enough in tension to resist the seam pulling apart in normal use. The relatively flexible thread need not be strong enough to allow the one or more stitches to be pulled out from one end of the tube, and may break or be at risk of breaking under such applied forces, especially if the thread is long or there are multiple stitches. The different characteristics of the relatively flexible thread and relatively rigid member are thus used to render each one suitable for its own purpose in forming a stitched seam that can be reliably released. Because each component is selected to have properties suited to its specific role, dimensions of the components can be reduced and overall size of the seam structure substantially minimised.

In preferred embodiments, the thread passes back to the first side from the second side through both layers of overlapped material. This helps to ensure the rigid member is appropriately constrained in position, at least in the lateral direction, on the second side. In one preferred form, the thread is formed as a loop on the second side, and passes back from the second side to the first side through the same hole through which it passes through the two layers from the first side to the second side. Besides constraining the relatively rigid member in position, this helps to ensure that the seam can be relatively easily pulled open when the rigid member is removed from within the loops on the second side, without the loops having to be pulled through the tube material to separate the seam.

In further preferred embodiments, the thread also crosses the relatively rigid member on the first side and passes again through both layers to the second side. This serves to prevent the stitches from being pulled through not only from the second side, on which the relatively rigid member is disposed, to the first side, but also in the reverse direction from the first side to the second side, thereby preventing unwanted release of the stitching.

In yet further preferred embodiments, the seam extends from the proximal end of the tube to the distal end of the tube. The seam can then be released along its whole length, which assists the tube of material to peel away from any implant carried within the tube.

In even further preferred embodiments, the seam extends substantially parallel to the central axis of the tube. This facilitates controlled and progressive release of the stitching by enabling the rigid member to be removed by controlled amounts corresponding to linear proximal inputs to retract the rigid member.

In yet even further preferred embodiments, a series of stitches are provided along the length of the seam. This can provide an even seam that is atraumatic during insertion of the tube in a body without snagging on lumen walls, and ensures a seal along the seam between the inside of the tube and outside it.

In still further preferred embodiments, the one or more stitches which cross the relatively rigid member are provided at least at the proximal or distal end of the seam. This allows progressive release of the stitching staring from one end, which will be most appropriate in most implant delivery applications.

In still even further preferred embodiments, the relatively rigid member is disposed on the second side along at least a proximal or distal portion of the seam. In certain applications, the rigid member need only be provided at the location where release of the stitching is to be initiated, where the release of stitching along the remaining length of the seam will propagate thereafter in a predictable and regular fashion.

In yet still further preferred embodiments, the relatively rigid member is a relatively rigid thread. As a relatively rigid thread, the relatively rigid member is able to inhibit release of the stitching when disposed between the stitches and the second side, but has a low profile which maintains an overall small diameter for the catheter and can extend beyond the tube to the proximal end of an associated device, where it can be manipulated to release the stitching.

In yet still even further preferred embodiments, the relatively flexible thread is of material which is more flexible than the material of the relatively rigid member. Threads can be made of differing flexibility by altering either the material from which they are formed or their size and construction. In seeking to keep dimensions to a minimum, it is preferred that appropriate different materials be used to give the relatively rigid member and relatively flexible thread their respective properties.

In more preferred embodiments, the relatively rigid member is disposed between the one or more stitches which cross it and the second side so as to be removable from between them by sliding in a direction substantially parallel either to the seam or to the central axis of the tube. Preferably, the relatively rigid member is removable by sliding under the application of a tensile force, and is substantially inextensible under the application of the tensile force. This allows the rigid member to be removed from the proximal or distal end of the tube by a simple pulling motion, for releasing the stitches. By the rigid member being inextensible, retractions at the proximal end are transmitted to the distal end simultaneously and with precision.

In yet more preferred embodiments, the relatively rigid member is of a shape memory or superelastic alloy, preferably a nickel-titanium alloy, or stainless steel. Shape memory alloys are particularly useful as they resist plastic deformation, returning to their memorised configuration after bending, and thus ensure the rigid member can reliably be withdrawn by simple sliding motion. These alloys, and stainless steel, are all strong under tension, and can therefore be made relatively thin whilst still being strong enough to function. Nickel-titanium alloys in particular have a failure mode at the point of breaking under tension that is advantageous; rather than extending substantially linearly with applied force to a point where the material suddenly fails, the material first reaches a point where it stretches by a substantial amount for little increase in applied force. This provides a warning to the person pulling on the relatively rigid member that it is about to break, rather than the member appearing to suddenly snap without warning. Thus, a defect or problem can be identified prior to critical failure, during the release process, allowing appropriate remedial action to be taken.

In still more preferred embodiments, the relatively flexible thread is of polymer and/or is a surgical suture thread. The relatively flexible thread has to be able to adopt a tight curve in order to form the stitches in the seam. Less rigid members are less suitable for stitching the overlapping layers together.

In even more preferred embodiments, the two edges of the tube material which meet and at least partially overlap along the seam are disposed on the inside of the tube. This keeps the outer surface of the tube of material smooth, and the tube of material is thereby effectively rendered atraumatic.

In yet even more preferred embodiments, the tube material is a polymer, preferably PTFE, PET, polyamide, polyethylene, or the like. These materials are not only suitable for use in devices where biocompatibility is required, but also allow the stitches to be released by being bulled through the material under application of an implant release force.

In still yet even more preferred embodiments, the tube is formed from a sheet of tube material. Although a larger-diameter tube of the tube material could be stitched along a seam formed by pushing together two internal edges along the inner wall surface, a sheet of material is preferably used to form the tube of material, as it can be accurately cut to size and stitched along the edges, thus being easily formed into a tube shape.

The present invention also provides an implant delivery catheter comprising a tube of material according to any above recitation of the first aspect of the invention.

In embodiments of the implant delivery catheter, the tube of material is an outer sheath provided over a distal portion the delivery catheter to house an implant mounted on an inner shaft at the distal portion of the delivery catheter. The tube protects and constrains the implant during delivery to the intended treatment location, as well as protecting the patient's body lumens from damage by the implant.

In further embodiments, the rigid member extends or is coupled to an actuator at the proximal portion of the delivery catheter, whereby the rigid member can be removed from between the one or more stitches which cross it and the second side of the overlapped tube material. The relatively rigid member can extend proximally beyond the length of the tube of material for connection to means for its withdrawal, such as a specially designed hand controller for removing the relatively rigid member from between the stitches which cross it and the second side.

In yet further embodiments, when the rigid member is between the one or more stitches which cross it and the second side of the overlapped tube material, the one or more stitches which cross it are inhibited from being pulled through the two layers of tube material under application of an implant release force, and, when the rigid member is removed from between the one or more stitches which cross it and the second side of the overlapped tube material, the stitches can be pulled through the two layers of tube material under application of an implant release force. Stitching across the rigid member on both sides of the overlapped tube material improves the integrity of the stitched seam and provides for a repeatable zig-zag pattern that can extend along all or part of the seam crossing the rigid member.

In even further embodiments, two or more stitches which cross the relatively rigid member are provided along at least a portion of the length of the seam, and the relatively rigid member is removable from between the two or more stitches in sequence, whereby an implant within the tube of material can be progressively released under application of the release force as the rigid member is sequentially removed. Progressive release of the implant allows one end of the implant to be positioned accurately, before the implant is fully released, followed by controlled release of the remainder of the implant. Thereby, the implant can be accurately placed at the delivery location, and trauma to the patient can be avoided by the controlled release without impinging on the patient's tissue.

In yet even further embodiments, the implant is of self-expanding material and is constrained in a delivery configuration within the tube of material against its tendency to expand to a release configuration, thereby imparting an implant release force to the tube of material. The tube of material is ideally suited to use with self-expanding implants, which will provide the necessary force to free themselves at the delivery location, once the rigid member is removed from the stitched seam. No further means for releasing the stitching then need be provided to the implant catheter.

In still preferred embodiments, the implant comprises a self-expanding stent. The tube of material is particularly suitable for use in percutaneous delivery applications, widely used for implanting stents, stent grafts and valve devices into patients' vasculature or other bodily lumens. In particular, the progressive release that can be obtained with the tube of material as the seam is unstitched is useful in accurate stent placement, and the stent itself can provide the necessary release force to pry open the tube of material as the rigid member is removed from the stitches.

According to a second aspect of the present invention, there is provided a method of manufacturing a tube of material comprising the steps of: —at least partially overlapping two ends of the tube material between proximal and distal ends; —disposing a relatively rigid member on a second side of an overlapping portion of the seam; and —forming a seam by stitching a relatively flexible thread from a first, opposite side of the overlapping portion of the seam, through both layers of the material, across the relatively rigid member on the second side and back to the first side. Such a manufacturing process is simple and can be carried out at relatively low cost using few components, yet provides a product that is effective in operation.

In preferred embodiments, stitching the relatively flexible thread includes passing the thread back to the first side from the second side through both layers of overlapped material. This ensures that the lateral position of the rigid member on the second side is fixed by the stitching, and serves to hold the stitched layers of tube material together.

In more preferred embodiments, stitching the relatively flexible thread further includes crossing the relatively rigid member on the first side and passing the thread again through both layers to the second side. A repetitive zig-zag stitching pattern can then be produced along at least a portion of the rigid member disposed on the second side. Crossing the stitching over the rigid member on the first side also improves the integrity of the stitched seam against the stitches being pulled through the layers of tube material in either direction.

In yet more preferred embodiments, forming the seam includes stitching the two ends of the tube material from the proximal end of the tube to the distal end of the tube. When the seam runs the whole axial length of the tube of material, the tube can be fully released to a non-tubular shape, facilitating release of an implant from within the tube. Stitching along the whole length of such a seam improves the evenness of the seam and provides a stronger seam to resist forces acting to separate the two overlapped layers of tube material.

In still more preferred embodiments, forming the seam includes stitching the two ends of the tube material substantially parallel to the central axis of the tube. When the seam is formed parallel to the tube axis, not only is it simpler to manufacture, but also the seam will be more uniform and even, and will tend not to be affected by forces transmitted longitudinally along the tube. Moreover, removal of the relatively rigid member from the stitches by sliding in the direction of the seam or tube central axis is facilitated.

In even more preferred embodiments, stitching the relatively flexible thread to cross the relatively rigid member on the second side is done at least at the proximal or distal end of the seam. This provides for the relatively rigid member to be removed at or from one end to release the stitching, and further release will then be predictable based on the stitching pattern, if any, used on remaining portions of the seam, or can be controlled by progressively removing the rigid member from stitches along the length of the seam, if such are provided to cross the rigid member along all or a significant part of the seam length.

Yet still more preferred embodiments further comprise the step of: —folding the stitched tube of material inside-out so that the two stitched edges of the tube material which meet and at least partially overlap along the seam are disposed on the inside of the tube. By initially forming the stitching on the outside of the tube, the rigid member can be stitched into the seam of overlapped tube material without having to access the seam from the inside of the tube. Turning the tube inside out to place the seam on the inside presents a relatively smooth and even, atraumatic outer surface of the tube in the seam region. The stitched seam material and relatively rigid member are contained inside the tube where they cannot impinge on and scratch or puncture the wall of a bodily vessel through which the tube would be advanced.

According to a third aspect of the present invention, there is provided a method of manufacturing a tube of material comprising the steps of: —at least partially overlapping two ends of the tube material between proximal and distal ends; —stitching a seam by passing a relatively flexible thread from a first side of an overlapping portion of the seam, through a hole through both layers of the material, to a second, opposite side of the overlapping portion to form a loop on the second side, whereby the thread of relatively flexible material passes back from the second side to the first side through the same hole through the two layers; and —disposing a relatively rigid member on the second side of the overlapping portion of the seam to extend through the loop.

In one preferred embodiment, stitching a seam includes forming a plurality of loops along the seam on the second side of the overlapping portion; and disposing a relatively rigid member on the second side of the overlapping portion includes disposing the rigid member to extend through substantially all of the loops. The stitching formed in this way can be released progressively by removing the rigid member from each loop in turn. With this method, a loop of the relatively flexible thread can be punched through the two overlapped layers of tube material or pushed through a pre-formed hole, and the rigid member is simply inserted to inhibit the loop of thread being pulled back through to the first side. Stitching formed in this way is easily released by removing the rigid member from the loop, allowing it to pass back through the hole and enabling the seam to separate.

In an alternative preferred embodiment, stitching a seam includes forming a series of loops along the seam on the second side of the overlapping portion, each loop in the series from one end passing through the next loop in the series whereby each next loop in the series is inhibited from being pulled through the hole through the two layers to the first side; and disposing a relatively rigid member on the second side of the overlapping portion includes disposing the rigid member to extend through at least the loop at the one end. The stitching formed in this way can be released simply by removing the rigid member from the loop at the one end, and progressive subsequent separation of the seam will occur as the loops in the series release each other sequentially.

BRIEF DESCRIPTION OF THE DRAWINGS

To enable a better understanding of the present invention, and to show how the same may be carried into effect, reference will now be made, by way of example only, to the accompanying drawings, in which: —

DETAILED DESCRIPTION

Specific embodiments of the present invention will now be described, with reference to the illustrated examples shown in the accompanying drawings. Reference to the drawings is made for illustrative purposes, and should not to be taken to be limiting of the scope of the claims.

In general, embodiments of a tube of material are formed by folding a sheet of the material so as to bring two edges of the material together to form a seam. Alternatively, a larger-diameter tube of the material may be pressed together to bring two portions of its internal surface together along its length, thereby forming a smaller-diameter tube with edges in a seam. The material from which the tube is made can be any suitable biocompatible material, as is well known to the person skilled in the art for such applications, including ePTFE, polyethers such as polyterephthalate (DACRON® or MYLAR®), or polyaramids such as KEVLAR®. Any other suitable polymer, fabric or a foil of metallic material may be used, as appropriate. Where suitable, the tube of material may be a composite comprising a combination of any of these materials, and may include a reinforcing structure, such as braiding or other wire reinforcement, as required.

The seam formed by bringing together two edges of the material is two or more layers thick, and is stitched to hold the seam together. The seam is preferably formed in such a way as to lie parallel to the central axis of the tube formed by stitching the seam, but may instead be formed as a non-parallel seam, for example extending helically around the wall of the tube between the proximal and distal ends. Likewise, the seam is preferably formed along the entire length of the eventual tube from the distal end to the proximal end, but may also be formed only along part of the longitudinal length of the tube between the proximal and distal ends. The seam is stitched by a relatively flexible thread which may be a surgical suture or any suitable polymer thread capable of adopting the configuration of closely-spaced, high curvature stitches. Suitable threads may be formed of ePTFE, polyethers or polyaramids, or may even be formed of a suitable biocompatible metal, such as Nitinol, stainless steel or gold, providing that the thread has the necessary high flexibility. The thread need only have sufficient strength under tensile forces to hold the seam together, and may therefore be made of a relatively weak material, or be made as relatively thin or small-diameter thread of strong material such Nitinol or stainless steel, to achieve the necessary degree of flexibility.

On one side of the seam, a relatively rigid member is provided interposed between one side of the seam and least one of the stitches formed by the relatively flexible thread. The relatively rigid member may also take the form of a thread and is preferably formed of a material such as stainless steel or a nickel-titanium alloy such as Nitinol®. These materials are biocompatible and have the necessary rigidity, whilst are strong under tension to enable the rigid member to be retracted proximally, even when formed as a thin thread. In other applications, however, the relatively rigid member may be formed of a less rigid material having a larger size or diameter to achieve the required overall rigidity.

By being relatively rigid, the relatively rigid member resists forces tending to deflect its shape, meaning that it will remain relatively straight during insertion of the tube of material along a curved passage way, facilitating its subsequent retraction out of the stitch or stitches which cross it on the side of the seam. The rigid member resists or inhibits the stitches of relatively flexible thread which cross it from being pulled through the seam, which would cause the stitching to come apart and allow the seam to open. Whereas the relatively flexible thread adopts a low radius high curvature configuration at the stitches, which inhibits it from being pulled out of the seam from one end, the relatively rigid member stays more aligned with the seam or the central axis of the tube of material, allowing it to be reliably retracted from its position between the seam and the stitches which cross it. Removing the relatively rigid member out from between the stitches and the side of the seam in this way will allow the stitches to come apart. In one variation, the stitches are formed so as to pass through the seam material through a first hole, to cross the relatively rigid member, and to pass back to the other side of the seam through a second different hole. With the rigid member removed, the relatively flexible thread is able to be pulled through the seam by tearing through the material interposed between the two separate holes. In another variation, the individual stitches are formed as loops which pass through a hole in the two layers of seam material, around the rigid member and back through the same hole in the two layers of material at the seam. In this way, there is virtually no resistance to the seam coming apart after the rigid member has been removed.

The use of a relatively rigid member and relatively flexible thread in combination in order to form the stitched seam can enable the stitching of the tube of material to be reliably released by retracting the rigid member in a proximal direction, with little or no risk of snapping the rigid member by this action due to its resistance to bending, which will inhibit snagging or tangling of the member between the stitched tube of material and the proximal end of the device, and due to the strength of the rigid member under tension, even when formed as a thin thread. The relatively flexible thread provides the necessary stitching, able to be released by removal of the rigid member but otherwise serving to provide a seam of sufficient strength to resist the seam coming apart under implant release forces which may be exerted prior to the rigid member having been removed.

Turning now to the drawings figures, reference is made to the specific illustrated embodiments, in which certain components are shown enlarge as compared with other components, for the purposes of clear exposition. It will be appreciated that the relatively flexible thread has been illustrated with the stitches formed loosely, in order to demonstrate clearly the stitching pattern used.

It will be appreciated that the various stitching patterns and rigid members which are illustrated may be used separately or in combination with one another, and that more than one illustrated stitching pattern can be used together along the same seam. Different portions of the seam may be provided with different stitching patterns, including those of the illustrated embodiments of the drawing figures.

Figures 1, 2, 3:
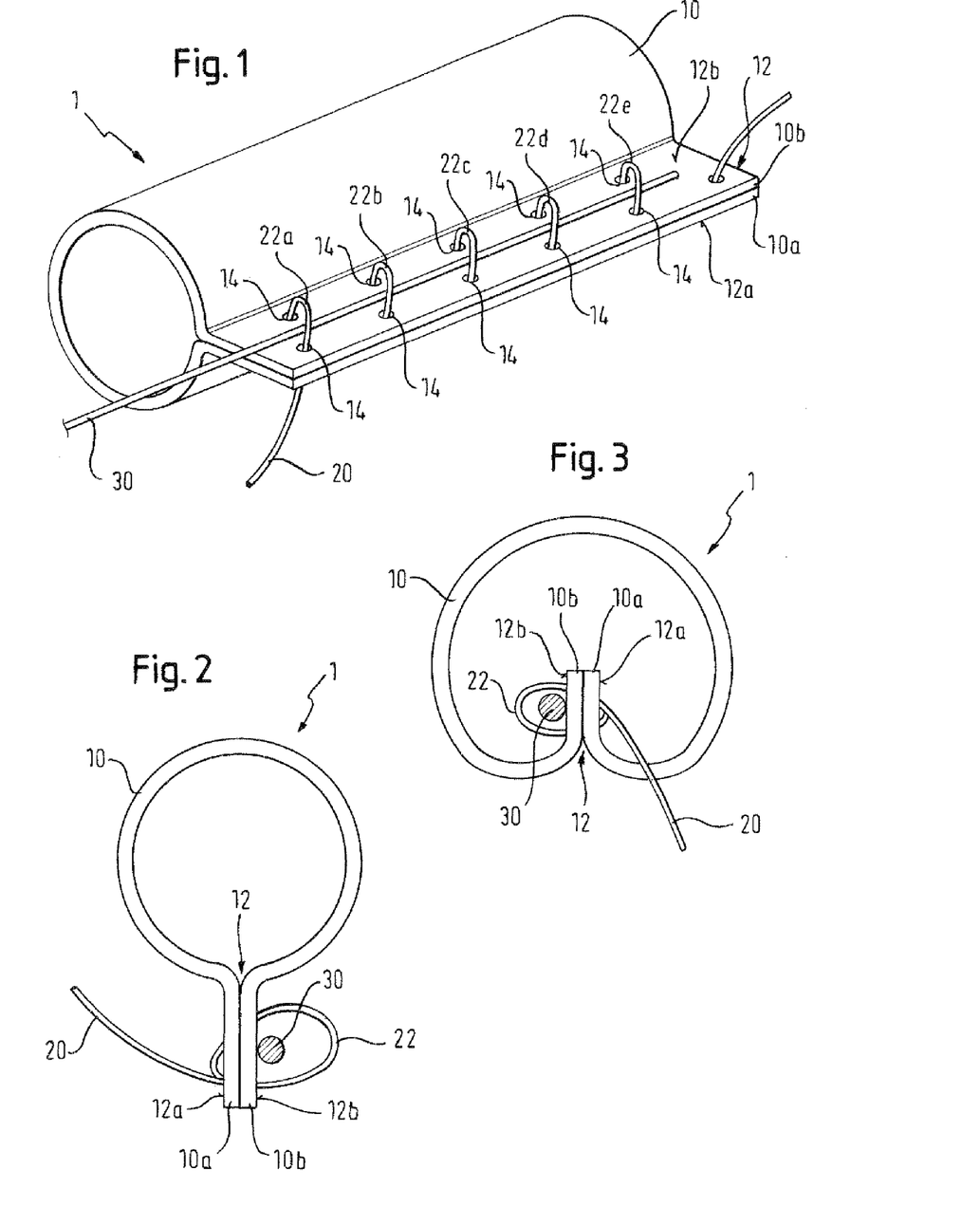
FIG. 1 shows a representative perspective view of a first embodiment of a tube of material according to the present invention.
FIG. 2 shows a representative end view of the first embodiment.
FIG. 3 shows a representative end view of the first embodiment after the tube of material has been turned inside-out.

In FIG. 1 there is illustrated a first embodiment of a tube of material 1 formed from a sheet of material 10. Two edges 10*a* and 10*h* of the sheet of material 10 are formed into a seam 12 where they overlap each other. A relatively rigid member 30 is disposed on a second side 12*b* of the seam 12, and extends from the seam in a proximal direction. A relatively flexible thread 20 passes, at the proximal end of the seam 12, from a first side 12*a* of the seam 12, through a hole 14 through both layers of the seam material, and crosses the relatively rigid member 30 on the second side 12*b* of the seam 12, before passing back through a second hole 14 through both layers of the seam 12, so as to form a stitch 22*a* at the proximal end of the seam 12. The relatively flexible thread 20 then crosses, on the first side 12*a* of the seam 12, back under the position of the relatively rigid member 30, which is on the second side 12*b* of the seam 12 before it passes again through a hole 14 through both layers of material in the seam 12 to emerge on the second side 12*b* of the seam. The relatively flexible thread 20 then passes again through a further hole 14 back to the first side, forming a second stitch 22*b* on the second side 12*b* of the seam 12. This stitching pattern is repeated along the length of the seam 12, to form a series of stitches 22*a-e*. It can be seen how, with the stitches 22*a-e* pulled tight, the rigid member 30 will be constrained in its lateral position, but will be free substantially to slide in proximal and distal directions parallel to the seam 12 or tube central axis.

FIG. 2 shows an end view of the tube of material 1, illustrating how the sheet of material 10 is formed into a tube having a seam 12. Of course, the sheet of material 10 can simply be folded in half for the purposes of stitching the seam 12, and will generally form a substantially cylindrical tube shape when an internal pressure, or a member exerting a radially outwards force, is provided inside the tube.

FIG. 2 further illustrates how the relatively flexible thread 20 passes through both layers of tube material in the seam 12, from the first side 12*a* to the second side 12*b*, and crosses the relatively rigid member 30 on the second side 12*b* to form a stitch 22, before passing back through both layers of the tube material to the first side 12*a*.

In practice, it is undesirable for the tube of material to have an outer surface with a seam which projects from the otherwise smooth surface of the tube, since the seam could damage the internal surface of a bodily lumen through which the tube of material is advanced, potentially scratching or rupturing the bodily lumen or dislodging plaque material from the inside surface of the lumen.

As illustrated in FIG. 3, the tube of material formed as shown in FIG. 2 is then preferably turned inside-out, so that the stitched seam 12, including the relatively rigid member 30 and the relatively flexible thread 20 is formed on the inside of the tube of material 1.

Because the relatively rigid member 30 is preferably made from a nickel-titanium alloy having super-elastic properties, it is able to withstand the process of being turned inside-out and will then return to its substantially straight configuration along the seam.

Figure 4:
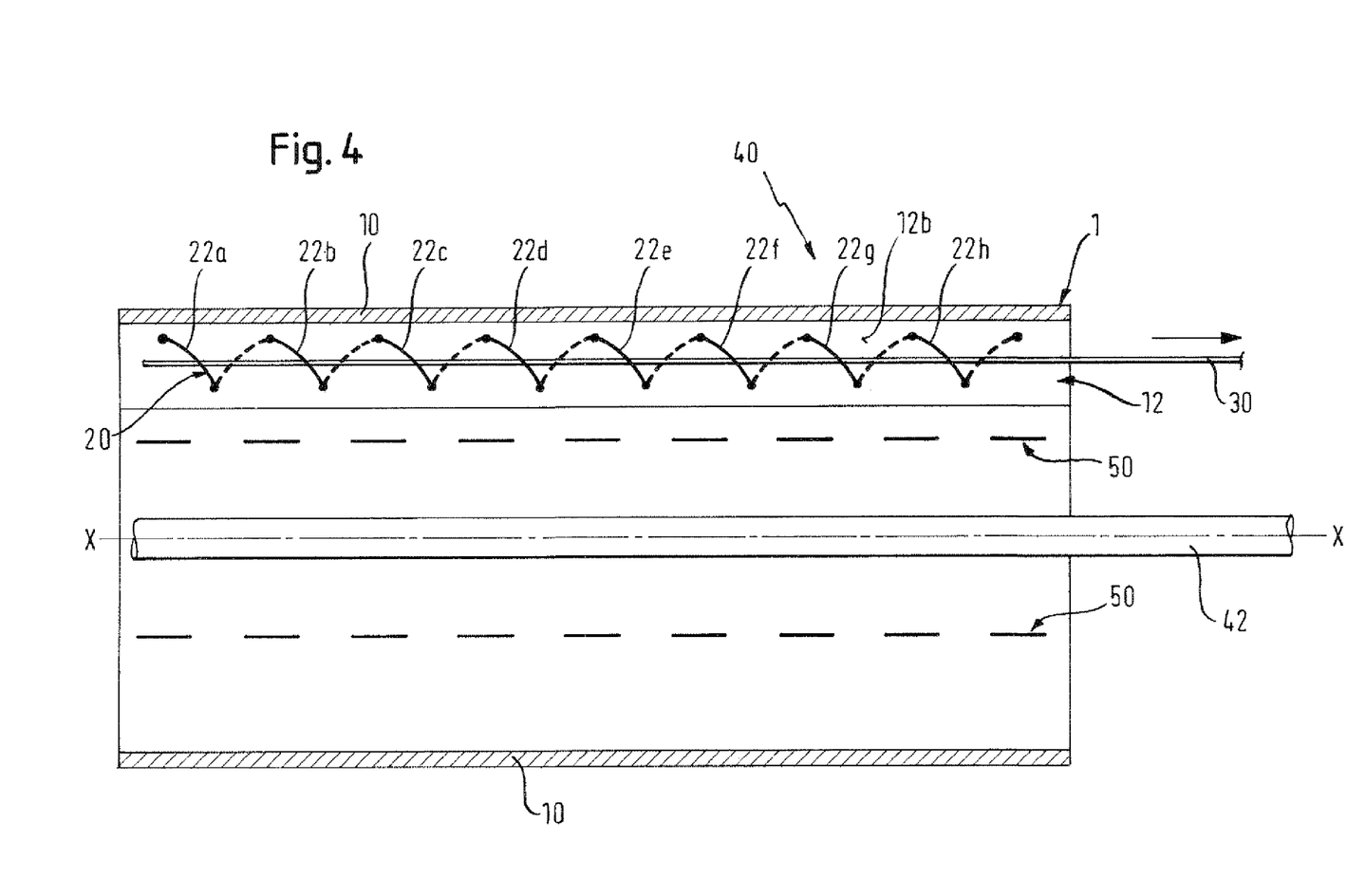
FIG. 4 shows a schematic illustration of an embodiment of an implant delivery catheter in which the tube of material of the first embodiment is incorporated.

FIG. 4 shows how a tube of material 1 formed in substantially the same manner as the tube of material shown in FIG. 3 is employed in an implant delivery catheter 40. Delivery catheter 40 is a system for delivering a stent 50 as the implant.

Implant delivery catheter 40 is provided with an inner shaft 42 extending from a proximal end of the catheter to a distal end, and having a central axis X-X. Stent 50 may be a self-expanding stent or stent graft and is mounted to the inner shaft 42 at a distal portion of the inner shaft 42, near to the distal end of the implant delivery catheter 40.

Tube of material 1 is formed substantially coaxially with the stent 50 to function as an outer sheath in the implant delivery catheter 40. Tube of material 1 therefore substantially completely covers the stent 50 to constrain it in its delivery configuration mounted to the inner shaft 42.

FIG. 4 illustrates how the seam 12, formed on the inside of the tube of material 1, is provided with a series of stitches 22*a-h*, which cross the rigid member 30 on the second side 12*b* of the seam 12. Rigid member 30 extends proximally from the tube of material 1 and extends along with the inner shaft 42 to a proximal end of the implant delivery catheter which will remain outside the body of a patient during an implant delivery procedure. Implant delivery catheters may be up to 150 cm long, and the relatively rigid member 30 is thus preferably formed of a material such as a nickel-titanium alloy or stainless steel, able to transmit tensile forces all the way from the proximal end of the delivery catheter 40 to the distal tip of the rigid member without snapping. At least the portion of the relatively rigid member 30 extending proximally from the tube of material 1 may be formed as a thin thread, able to adapt to the natural curvature of the bodily lumens through which the implant delivery catheter 40 may be advanced, but being relatively rigid to resist adopting high curvature, low radius configurations similar to the stitches 22*a-h* formed from the relatively flexible thread 20.

Although the relatively rigid member 30 and the relatively flexible thread 20 are preferably both formed as threads of relatively rigid and flexible materials, respectively, it is of course possible to form both the rigid member 30 and the flexible thread 20 from the same material, but to make the rigid member 30 substantially larger in shape or diameter so as to provide it with the increased rigidity as compared with the relatively flexible thread 20.

Although in the example of FIG. 4 the stent 50 is provided as a self-expanding stent, the implant delivery catheter 40 could alternatively be a balloon catheter, having a balloon mounted along the portion of the inner shaft 42 to which the stent is mounted, the balloon being inflatable to deploy the stent 50 and to force open the seam 12 of the tube of material 1, after the relatively rigid member 30 has been removed from the stitches 22*a-h*.

The further illustrated embodiments are variation on the embodiment of FIGS. 1 to 3, and may be used in the implant delivery catheter of FIG. 4 in place of the tube of material 1 illustrated therein.

Figure 5:
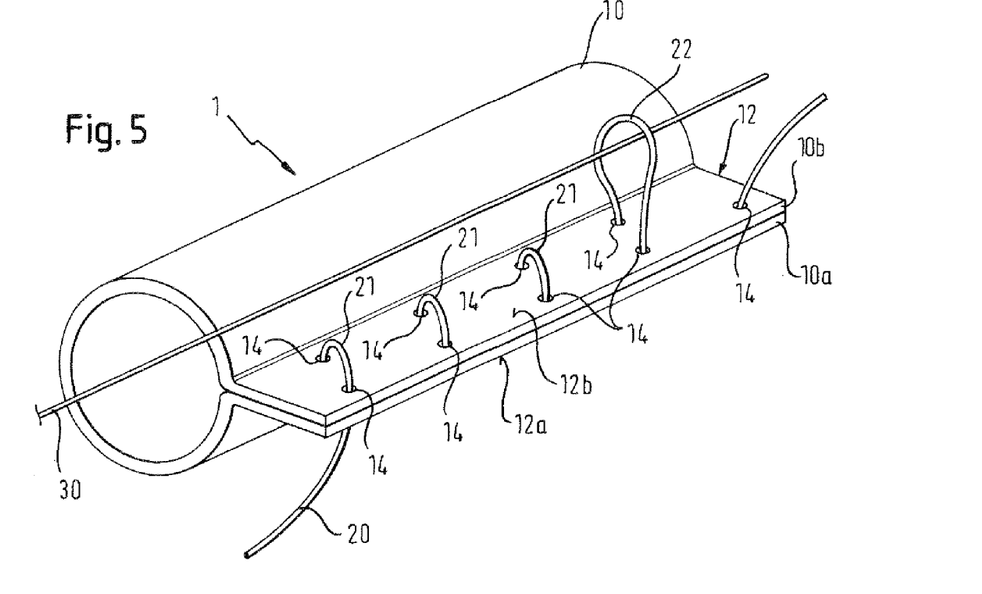
FIG. 5 shows a representative perspective view of a second embodiment of a tube of material according to the present invention.

In the embodiment shown in FIG. 5, the tube of material 1 is formed from a sheet 10 folded so that edges 10*a* and 10*b* meet to form a seam 12 which is two layers thick. A flexible thread 20 is provided, passing from the first side 12*a* to the second side 12*b* of the seam through both layers of material and then back again, through holes 14 formed through the two layers of the seam 12, to form a series of stitches 21 along the seam 12. A single stitch 22 is formed at one end of the seam 12 to cross the relatively rigid member 30, the relatively rigid member 30 preventing this stitch 22 from being pulled through the seam 12 to release the stitching. The one stitch 22 which crosses the relatively rigid member need not be a single stitch, it being possible to provide one or more stitches 22 which cross the rigid member 30, as well as one or more stitches 21 which do not cross the rigid member 30, along the second side 12b of the seam 12. Such a stitching arrangement may be used where the tube of material 1 has a tendency to open from one end, the relatively rigid member 30 serving the secure the stitch 22 against opening at that end, and whereby removal of the rigid member 30 allows the stitched seam 12 then to open sequentially from the one end as the stitches 21 come apart one-at-a-time, thus releasing an implant from within the tube of material 1 in a progressive fashion.

Figure 6:
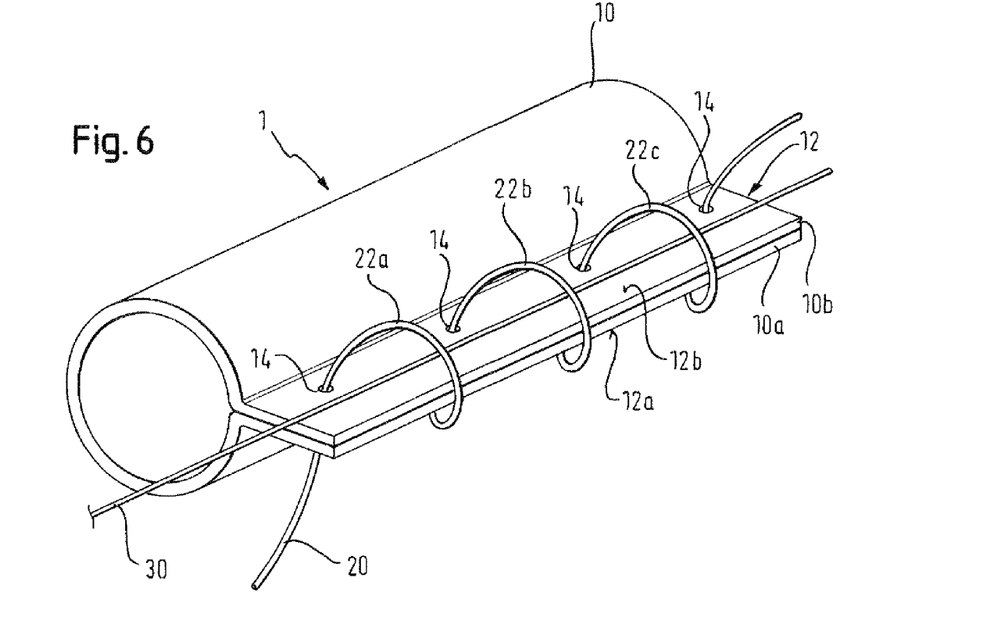
FIG. 6 shows a representative perspective view of a third embodiment of a tube of material according to the present invention.

FIG. 6 shows a tube of material 1 formed from a sheet of material 10 folded to produce a seam 12 where the edges 10a and 10b of the sheet come together. The relatively flexible thread 20 forms a series of stitches 22a-c by passing from the first side 12a of the seam 12 through both layers of material to the second side 12b through a hole 14 through both layers. The flexible thread 20 then crosses the relatively rigid member 30 on the second side 12b of the seam 12, before passing back to the first side 12a of the seam 12 around the edges 10a and 10b of the sheet of material 10, without passing back through the two layers of the seam material. This form of stitching is repeated to form the series of stitches 22a-c along the length of the seam 12.

Figure 7:
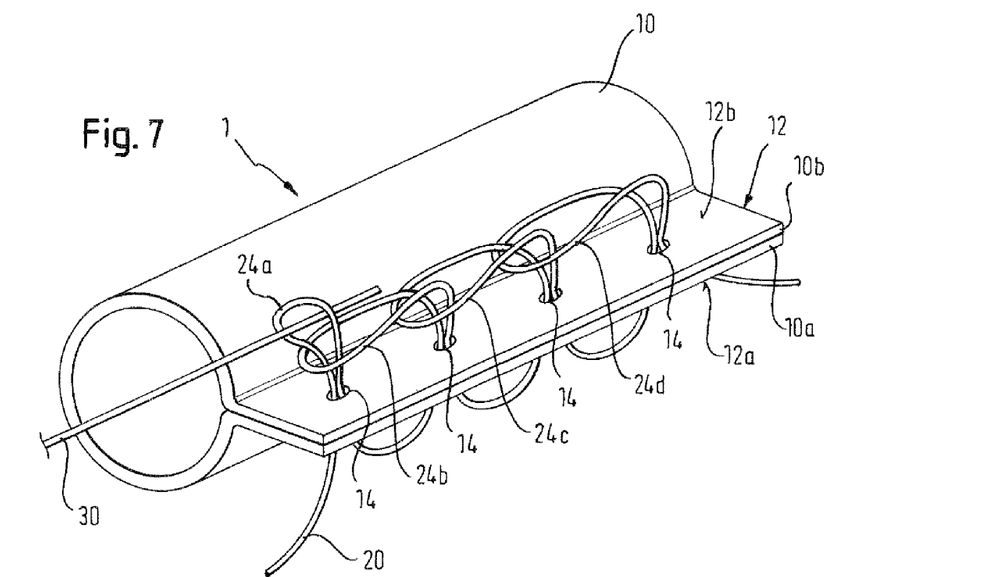
FIG. 7 shows a representative perspective view of a fourth embodiment of a tube of material according to the present invention.

FIG. 7 shows an embodiment of a tube of material 1 formed from a sheet of material 10 to have a seam 12 which is two layers thick where the edges 10a and 10b of the sheet of material 10 come together. A series of holes 14 are formed through both layers of the seam 12, along its length. A stitching pattern is formed by passing loops 24a-d of the relatively flexible thread 20 through each of the holes 14 in the seam. Each loop 24a-c in the series of loops 24a-d passes through the next loop 24b-d in the series, on the second side 126, to effectively lock the loops 24a-d together on the second side 12b of the seam 12 as a series of stitches. The relatively rigid member 30 then passes through the first loop 24a in the series, to lock this first loop against being pulled through the hole 14 in the seam 12, thereby securing the stitching along the entire interlocked length of loops of stitches 24a-d.

In this way, the stitches 24a-d are held firmly in place until the relatively rigid member 30 is removed from the first loop 24a, allowing the loop 24a to be pulled back to the first side 12a of the seam 12 through the hole 14 through both layers of the seam 12. This then releases the second loop 24b to pass back through the next hole 14 in the seam, thus facilitating progressive sequential release of the seam 12 and allowing the tube of material 10 to open along the seam 12 in a progressive fashion from one end. The loop 24a which is locked in place by the rigid member 30 may of course be provided at either end of the seam 12, or may be provided in a centre portion of the seam 12, if it is desired to provide a seam 12 which opens from the centre progressively outwardly towards each end thereof.

Figure 8:
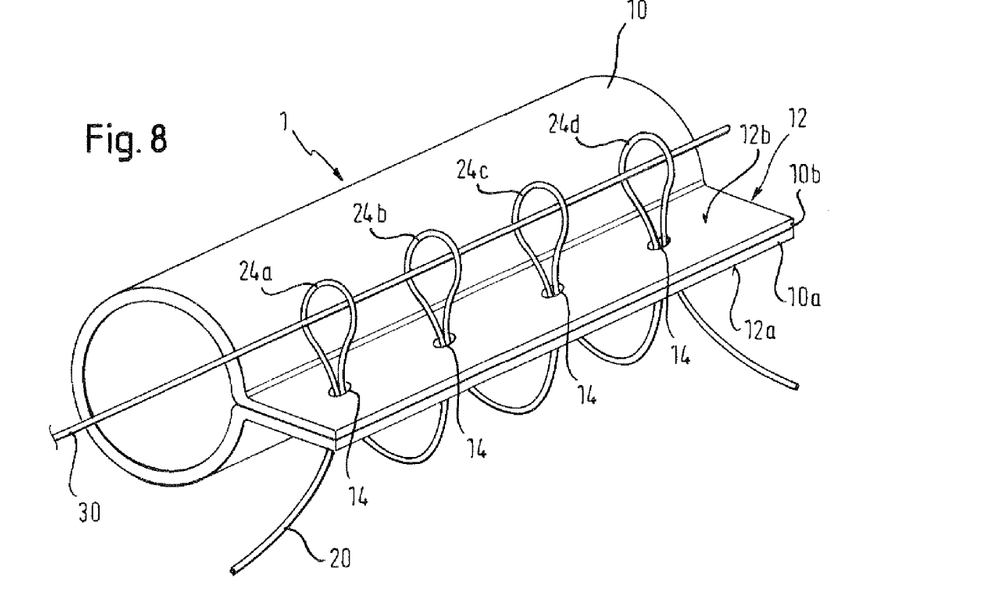
FIG. 8 shows a representative perspective view of a fifth embodiment of a tube of material according to the present invention.

FIG. 8 shows another embodiment of the tube of material 1 formed from a sheet of material 10 folded to make a seam 12 where two edges 10a and 10b of the sheet 10 come together, and having a series of holes 14 formed through both layers of the seam 12 along its length. Loops 24 of the relatively flexible thread 20 are pushed through each hole 14 through the two layers of material in the seam 12, to form a series of loop stitches 24a-d along the length of the seam. Relatively rigid member 30 is inserted through each loop in the series, to lock it against being pulled back through the seam 12 from the second side 12b to the first side 12a. When the relatively rigid member 30 is retracted to remove the member from each loop 24d-a in sequence progressive and controlled sequential release of the stitching along the length of the seam 12 is achieved. Thus, the seam 12 may come apart up to the point of the last-released stitch, but is still held closed at the point where the next stitch in series is locked by the relatively rigid member 30.

This facilitates progressive controlled release of an implant from within the tube of material 1, which aids in the accuracy of implant placement during a medical procedure, which is often of benefit when deploying stents along a length of a bodily lumen, in particular to ensure that the first positioned end of the stent or stent graft is correctly located.

Figure 9:
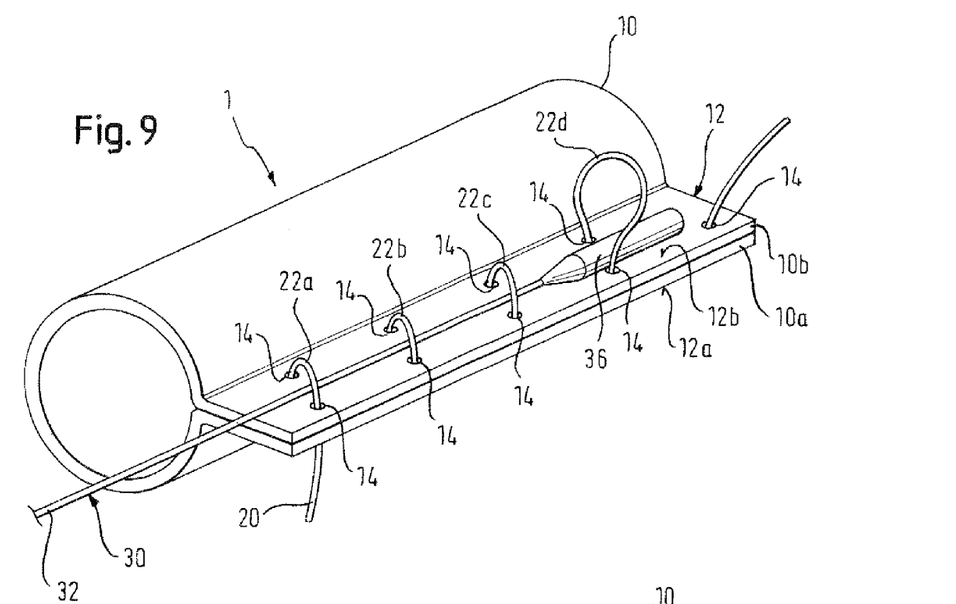
FIG. 9 shows a representative perspective view of a sixth embodiment of a tube of material according to the present invention.

FIG. 9 shows an embodiment of a tube of material 1 formed from a sheet of material 10 by folding the sheet so that opposite edges 10a and 10b meet to form a two-layer seam 12 along the length of the tube 1. A series of stitches 22a-d are formed along the length of the seam 12, to cross the relatively rigid member 30 on the second side 12b of the seam 12, in the same manner as in the first embodiment of FIG. 1. In the embodiment of FIG. 9, the relatively rigid member 30 is formed from a first, proximal section 32 formed as a small diameter thread extending proximally from the tube of material 1, and having a stitch releasing tip 36 formed at the distal end thereof. Stitch releasing distal tip 36 is formed as a larger-diameter end portion of the relatively rigid member 30, having a tapered transition between the small-diameter thread portion 32 and the larger-diameter portion 36. As the relatively rigid member 32 is retracted proximally to remove it from between the stitches 22a-d and the second side 12b of the seam, along the length of the seam 12, the stitch releasing tip 36 serves to pull apart each stitch 22d-a in turn, as the tapered portion and large diameter portion 36 are pulled through the stitches 22a-d, as illustrated schematically for the stitch 22d in FIG. 9.

Stitch releasing tip 36 might alternatively be provided as a cutting member, for cutting open each stitch in turn, in order to release the seam 12 to open along its length as the relatively rigid member is proximally retracted.

Figure 10:
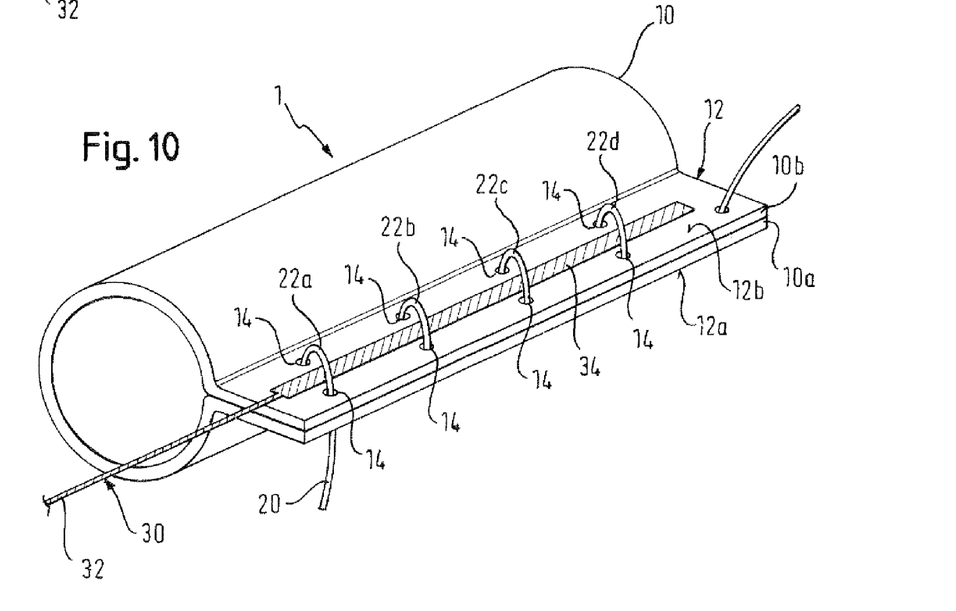
FIG. 10 shows a representative perspective view of a seventh embodiment of a tube of material according to the present invention.

FIG. 10 shows an embodiment of a tube of sheet material 1 formed from a sheet of material 10 folded to bring together opposite edges 10a and 10b to form a two-layer seam 12 along the length of the tube 1. Stitches 22 are formed from a relatively flexible thread 20 to provide a series of stitches 22a-d which cross relatively rigid member 30 on second side 12b of the seam 12 along the length thereof. In this embodiment, the relatively rigid member 30 is provided with a thread-like proximal portion 32 which extends proximally of the tube of material 1, and a wider rigid portion 34 which is positioned along the length of the seam 12. The rigidity of the relatively rigid member 30 is thus increased at the distal portion where it lies between each stitch 22a-d and the second side 12b of the seam 12, improving resistance to bending and facilitating smooth proximal retraction to remove the relatively rigid member 30 from between the stitches 22a-d and the second side 12b of the seam 12. Proximal thread-like portion 32 provides the necessary flexibility for adopting a curvature in line with the tortuous shape of a body cavity as the tube of material 1 is advanced through a bodily lumen such as the human vasculature.

In the forgoing embodiments, and in embodiments of the invention in general, it will appreciated that the holes 14 formed through the two layers of the seam 12 can in every case either be formed in advance of threading the relatively flexible thread 20 therethrough, such as by mechanical punching or using a laser, or they may be formed using a needle in a conventional stitching fashion.

Methods of manufacturing the tube of material 1 according to the forgoing embodiments include folding the sheet of material 10 to form a seam 12 where the two edges 10a and 10b of the material overlap; disposing relatively rigid member 30 on the second side 12b of the two overlapped edges of the tube material in the seam 12; and then stitching the relatively flexible thread 20 along the length of the seam 12 to form the stitches 22 which cross the relatively rigid member 30. An alternative method involves folding the sheet of material 10 to bring the opposite edges 10a and 10b together as a two-layer seam 12; forming a loop 24 or loops 24a-d of material through holes 14 through the two layers of material in the seam 12; and then inserting the rigid member 30 through each loop of material along the seam 12 after it is formed on the second side 12b of the seam 12. As necessary, each loop of material may then be pulled tight, once the rigid member 30 has been inserted.

In embodiments such as that shown in FIG. 7, each loop 24 is formed in turn, starting with loop 24d, with each subsequent loop 24c-a being passed through the loop 24d-b previously formed, to lock the loops 24a-d together, until the end loop 24a is formed and can be locked in position by the relatively rigid member 30.

In order to release the implant from within the tube of material 1 in an implant catheter device 40 such as that shown in FIG. 4, it will normally be necessary simply to retract the rigid member 30, after which the restoring force of the self-expanding implant or a radially outward implant release force, for example imparted by a balloon of a balloon catheter, will be sufficient to pull apart the seam 12. In certain embodiments, however, it may be preferable to extend the relatively flexible thread 20 proximally from the tube of material 1, so that it can be pulled to assist in releasing the stitches after the relatively rigid member 30 has been removed.

Figure 11:
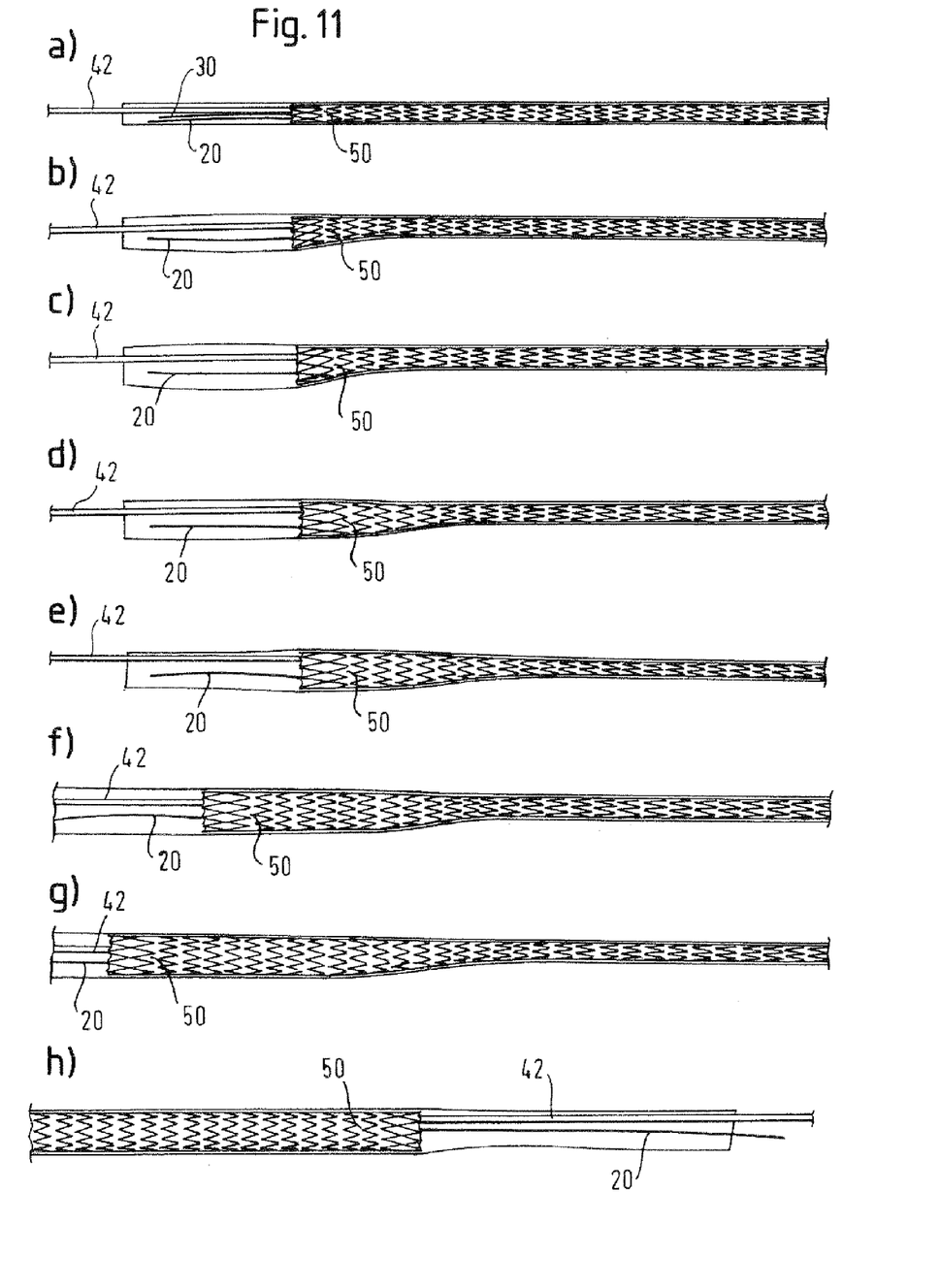
FIG. 11 is a series of pictures showing a sequence of steps a) to h) in the release of a self-expanding stent graft from an embodiment of an implant delivery catheter having a tube of material according to the present invention.

FIG. 11 shows a sequence of steps a) to h) in the release of a stent 50 mounted to an inner shaft 42 delivery implant catheter. The stent is a self-expanding stent 50 constrained in a delivery configuration by a transparent tube of material which surrounds it. The transparent tube of material is stitched together by a relatively flexible thread 20, which can be seen extending from the distal end of the tube of material 1. Also visible in step a) of the sequence is the relatively rigid member 30, projecting from the distal end. In the sequence of steps a) to h), the relatively rigid member 30 is gradually proximally retracted, and it will be appreciated how this results in the progressive release of the self-expanding stent 50 as the relatively rigid member 30 is removed from the distal end to the proximal end of the tube of material 1.

It will also be appreciated how the self-expanding stent 50 is incorporated into a stent graft, having a polymeric lining formed, for example, from ePTFE, to form a covered stent graft in the expanded operative configuration. It is moreover visible how the expanded diameter of the stent 50 is in the region of 3 times the diameter of the delivery configuration, although larger expansion ratios have been achieved with similar types of stent.

It will be appreciated how the spacing of the stitches affects the release behaviour of an implant from within the tube of material 1. Where the adjacent stitches 22 are relatively widely spaced, the implant release force exerted by a self-expanding stent located within the tube of material 1 which each stitch has to resist is relatively large, since each stitch 22 must hold the seam together against the expansion force of the stent 50 corresponding to a relatively long length of the stent. This can ensure that the stent has a sufficiently large restoring force to pull the relatively flexible material 20 through the two layers of tube material in the seam, by tearing the relatively small piece of tube material between the closely spaced holes through which the two sides of the stitch 22 pass through the tube material. The stitches 22 may of course be spaced more closely or at greater distance, depending on the strength of the tube material to resist tearing, and depending on the strength of the implant releasing force which will act to pull the seam apart to release the implant.

The spacing of the stitches will also have an effect on the release behaviour of the stent even where the loops 24 of relatively flexible material 20 pass through the same hole 14 and the stent 50 does not need to cause the flexible material 20 to rip through the seam 12 for its release. The release of the stent 50 will still be progressive, as each stitch is released in turn, and the distance between adjacent stitches will affect the smoothness of and ability to control the release, with closer stitches 22 or loops 24 providing a smoother, more gradual release.

The invention claimed is:

1. A tube of material configured for use with an implant delivery catheter, the tube of material having a seam extending between a proximal end and a distal end, two edges of the material meeting and at least partially overlapping along the seam and being sewn together at the seam by stitches of flexible thread, the thread of one or more of the stitches passing from a first side of the overlapped edges of material, through both layers of overlapped material, crossing over a rigid member which is disposed on a second, opposite side of the overlapped edges of material, and passing back to the first side, wherein the rigid member is relatively more rigid than the flexible thread.

2. The tube of material according to claim 1, wherein the thread passes back to the first side from the second side through both layers of overlapped material.

3. The tube of material according to claim 2, wherein the thread is formed as a loop on the second side, and passes back from the second side to the first side through a hole through which it passes through the two layers from the first side to the second side.

4. The tube of material according to claim 1, wherein the thread also crosses the rigid member on the first side and passes again through both layers to the second side.

5. The tube of material according to claim 1, wherein the rigid member is a rigid thread.

6. The tube of material according to claim 1, wherein the rigid member is disposed between the one or more stitches which cross it and the second side so as to be removable from between them by sliding in a direction substantially parallel either to the seam or to a central axis of the tube.

7. The tube of material according to claim 1, wherein the rigid member material is selected from the group consisting of a shape memory alloy, a superelastic alloy, a nickel-titanium alloy, stainless steel, or combinations thereof.

8. The tube of material according to claim 1, wherein the two edges of the tube material which meet and at least partially overlap along the seam are disposed on the inside of the tube.

9. An implant delivery catheter, wherein the tube of material according to claim 1 is an outer sheath provided over a distal portion of the delivery catheter to house an implant mounted on an inner shaft at the distal portion of the delivery catheter.

10. The implant delivery catheter according to claim 9, wherein the rigid member is coupled to an actuator at a proximal portion of the delivery catheter, wherein the rigid member can be removed from between the one or more stitches which cross it and the second side of the overlapped material.

11. The implant delivery catheter according to claim 10, wherein, when the rigid member is between the one or more stitches which cross it and the second side of the overlapped tube material, the one or more stitches which cross it are inhibited from being pulled through the two layers of tube material under application of an implant release force, and, when the rigid member is removed from between the one or more stitches which cross it and the second side of the overlapped tube material, the stitches can be pulled through the two layers of tube material under application of the implant release force.

12. The implant delivery catheter according to claim 11, wherein two or more stitches which cross the rigid member are provided along at least a portion of the length of the seam, and the rigid member is removable from between the two or more stitches in sequence, whereby an implant within the tube of material can be progressively released under application of the implant release force as the rigid member is sequentially removed.

13. The implant delivery catheter according to claim 12, wherein the implant is a self-expanding stent constrained in a delivery configuration within the tube of material against its tendency to expand to a release configuration, wherein the implant release force is imparted to the tube of material.

14. The tube of material according to claim 1, wherein the thread forms multiple loops along the seam, each loop of the multiple loops comprising the thread passing from the first side through a hole in the two layers to the second side, crossing over the rigid member, and passing back from the second side to the first side through a same hole, wherein each loop of the multiple loops is associated with a different hole in the two layers.

15. The tube of material according to claim 14, wherein only the rigid member extends through the multiple loops.

16. The tube of material according to claim 14, wherein the multiple loops include at least four different loops, each loop passing through one of four different holes.

17. The tube of material according to claim 1, wherein the flexible thread is flexible enough to adopt a small radius curvature to form the stitches, and wherein the rigid member is rigid enough to resist small radius, high curvature deflection.

18. The tube of material according to claim 1, wherein the flexible thread is strong enough in tension to resist the seam pulling apart in normal use, but is weak enough that the thread is likely to break before releasing the full seam if the thread is pulled from one end of the tube.

19. The tube of material according to claim 1, wherein the rigid member is only provided at a location where release of the stitches is to be initiated without extending along a full length of the seam from end to end.

20. The tube of material according to claim 1, wherein the rigid member is disposed on an outer surface of the second, opposite side of the overlapped edges of material such that the rigid member is only in direct contact with one of the overlapped edges.

* * * * *